(12) United States Patent
Moussou et al.

(10) Patent No.: US 9,949,917 B2
(45) Date of Patent: Apr. 24, 2018

(54) **COSMETIC COMPOSITION COMPRISING A COMBINATION OF A SUGAR FATTY ACID ESTER WITH A PLANT EXTRACT OF *WALTHERIA INDICA* OR *PISUM SATIVUM* FOR SKIN WHITENING**

(75) Inventors: Philippe Moussou, Tomblaine (FR); Louis Danoux, Saulxures les Nancy (FR); Laurent Bailly, Essey les Nancy (FR); Véronique Gillon, Essey les Nancy (FR)

(73) Assignee: Cognis IP Management GmbH, Düsseldorf (DE)

( * ) Notice: Subject to any disclaimer, the term of this patent is extended or adjusted under 35 U.S.C. 154(b) by 271 days.

(21) Appl. No.: 12/294,203

(22) PCT Filed: Mar. 14, 2007

(86) PCT No.: PCT/EP2007/002221
§ 371 (c)(1),
(2), (4) Date: Sep. 23, 2008

(87) PCT Pub. No.: WO2007/107268
PCT Pub. Date: Sep. 27, 2007

(65) Prior Publication Data
US 2009/0110651 A1    Apr. 30, 2009

(30) Foreign Application Priority Data

Mar. 23, 2006 (EP) ..................... 06005974

(51) Int. Cl.
*A61K 8/97* (2017.01)
*A61K 8/60* (2006.01)
*A61Q 19/02* (2006.01)

(52) U.S. Cl.
CPC .................. *A61K 8/97* (2013.01); *A61K 8/60* (2013.01); *A61Q 19/02* (2013.01)

(58) Field of Classification Search
None
See application file for complete search history.

(56) References Cited

U.S. PATENT DOCUMENTS

| | | | | |
|---|---|---|---|---|
| 4,900,555 A | * | 2/1990 | Cheng et al. | 424/449 |
| 5,747,049 A | * | 5/1998 | Tominaga | 424/401 |
| 6,184,199 B1 | | 2/2001 | Gilles | |
| 6,406,720 B1 | | 6/2002 | Gilles | |
| 2002/0076450 A1 | * | 6/2002 | Pauly et al. | 424/725 |
| 2002/0160061 A1 | * | 10/2002 | Saliou et al. | 424/757 |
| 2003/0152536 A1 | * | 8/2003 | Pauly et al. | 424/62 |
| 2005/0220726 A1 | | 10/2005 | Pauly | |

FOREIGN PATENT DOCUMENTS

| | | |
|---|---|---|
| EP | 1340486 A1 | 3/2003 |
| JP | 07173046 A * | 7/1995 |
| JP | 10033152 A * | 2/1998 |
| JP | 2002029929 A * | 1/2002 |
| JP | 2002-265348 | 9/2002 |
| JP | 2003/521505 | 7/2003 |
| WO | 98/55087 A1 | 12/1998 |

OTHER PUBLICATIONS

"Introduction of Sugar Esters". Internet Archive Date: Jun. 8, 2002 [Retrieved from the Internet on: Jan. 14, 2010]. Retrieved from: <http://web.archive.org/web/20020608171029/http://www.mfc.co.jp/english/whatsse.htm>.*

Sen, R. ed. "Synthesis of Sugar Esters" from "Biosurfactants". (2010), pp. 293.*

Encyclopedia of Polymers and Thickeners for Cosmetics Robert Y. Lochhead, PhD and William R. Fron vol. 108, May 1993, pp. 95-135.

* cited by examiner

Primary Examiner — Amy L Clark
(74) Attorney, Agent, or Firm — Marshall, Gerstein & Borun LLP

(57) ABSTRACT

The invention is directed to a skin-whitening agent comprising at least one sugar fatty acid ester and at least one plant extract selected from the group consisting of extracts of *Waltheria indica*, extracts of *Pisum sativum* and mixtures thereof. The invention is further directed to cosmetic compositions comprising such a skin-whitening agents.

11 Claims, No Drawings

COSMETIC COMPOSITION COMPRISING A COMBINATION OF A SUGAR FATTY ACID ESTER WITH A PLANT EXTRACT OF *WALTHERIA INDICA* OR *PISUM SATIVUM* FOR SKIN WHITENING

CROSS REFERENCE TO RELATED APPLICATIONS

This application is the National Phase entry of PCT/EP2007/002221, filed Mar. 14, 2007, which claims priority to EPO patent application number EP 06005974.8, filed Mar. 23, 2006, both of which are incorporated herein by reference in their entireties.

FIELD OF THE INVENTION

The present invention relates to cosmetic compositions for skin whitening, and more particular to a skin whitening active comprising sugar fatty acids esters and a plant extract selected from the extracts of *Waltheria indica, Pisum sativum* and mixtures thereof.

There is a global market demand for whitening agents in cosmetics to prevent and/or decrease abnormal pigmentations, such as freckles or spots are pigmentation due to over exposure to sun. Additionally some dark-skinned individuals prefer lighter skin colour which is regarded as a particular beauty feature.

BACKGROUND OF THE INVENTION

Many chemicals are well known for skin whitening activities, as hydroquinone, kojic acid, arbutin and ascorbic acid derivatives. However, the safety, stability, smell, or efficacies of these whitening agents do not satisfy consumers needs.

WO 02/053121 (LG Household & Healthcare Company) discloses glucose- and sucrose-esters with fatty acids having a carbon chain length of C3 to C6 and their use in cosmetics for skin whitening. WO 03/074013 and EP 1 340 486 A1 (Cognis France S. A.) discloses the use of sugar fatty acid esters as inhibitors of the melanin synthesis in hair and skin cells.

When trying to achieve a highly effective skin whitening activity in a cosmetic composition, the use of fatty acid esters is limited due to their emulsifying properties. Thus with sugar fatty acids the skin whitening activity that can be achieved in standard cosmetic formulations is limited.

WO 98/55087 (Laboratories Serobiologiques) describes cosmetic compositions comprising an extract from *Waltheria indica*. The anti-UV A, anti-UV B and the anti-collagenase effects, anti-ageing, anti-elastase, anti-radical and glutathione auto-synthesis reducing activity are disclosed. WO 01/056541 (=EP 1 253 906 B1) (Cognis France S. A.) describe cosmetic compositions containing extracts of *Waltheria indica* in combination with ferulic acid. WO 01/056541 discloses that these mixtures can be used as skin whiteners and as tyrosinase inhibitors, it does not disclose that *Waltheria indica* extracts alone, or in combination with any other component, display tyrosinase inhibiting activity in melanocytes (i.e. acting through a decrease of cellular tyrosinase activity and not as direct tyrosinase inhibitors).

It is preferred that skin whitening cosmetic compositions themselves are white or of a very light colour. When trying to achieve a highly effective skin whitening activity in a cosmetic composition, the use of plant extracts is limited due to the colour of the plant extracts.

Aim of the invention was to provide a skin whitening active which overcomes the draw-backs of the prior art. Of special interest was that a highly effective skin whitening active can be easily incorporated into cosmetic composition e.g. without developing or adjusting the emulsifier system for each formulation; e.g. not to contribute to the colour of the final formulation; e.g. not to require a concentration which interferes with the formulation of the cosmetic composition, thus being highly effective at low concentrations. In addition it is desired that the skin whitening active does not or only to a much lower extend than products known in the market, cause an irritation of the skin onto which it is applied.

It has surprisingly be found, that the skin whitening active of the invention can be formulated at a highly efficient concentration in cosmetic compositions. It has been found the skin whitening active can be easily formulated into a broad range of cosmetic compositions (e.g. W/O emulsions, O/W emulsions) and that it—at the same time—leads to very lightly coloured, in some cases even colour-less end products. In addition the skin whitening active of the invention does not show any irritation on the skin.

The skin whitening actives according to the invention allow to formulate cosmetic compositions which are highly effective in skin whitening, show very little colour and can be formulated in a wide range of cosmetic formulations types, e.g. W/O emulsions or O/W emulsions without special requirement to the emulsion system.

DETAILED DESCRIPTION OF THE EMBODIMENTS

The present invention relates to a skin-whitening active comprising
  (a) at least one sugar fatty acid ester
  (b) at least one plant extract selected from the extracts of *Waltheria indica* (b-1) or the extracts of *Pisum sativum* (b-2) and mixtures thereof.

It has surprisingly been found, that—even though extracts of *Waltheria indica* or extracts of *Pisum sativum* alone do not display tyrosinase inhibitory activity, they increase the tyrosinase inhibiting activity of sugar fatty acid esters. This makes it possible to formulate highly effective skin-whitening actives and skin-whitening cosmetic compositions.

The term "skin whitener" as used throughout the invention encompasses any cosmetic application which aims at changing the colour/pigmentation of skin to a colour which is lighter as compared to the state before the treatment with the skin whitener. The use as skin whitener thus encompasses the removal of pigmentation, e.g. spots and/or freckles, hyper-pigmentations which might be caused by exaggerated sun exposure but also the lightening of the cited pigmentations, e.g. changing the skin tone to a lighter one or lightening of freckles etc.

The term "skin whitener" as used throughout the invention also encompasses any cosmetic application which aims at preventing/avoiding a colouring/pigmentation of skin to a colour which is darker than the original skin tone. Examples of such use are sun-filters cosmetics.

The invention encompasses skin-whitening actives as well as cosmetic compositions comprising the skin-whitening actives,
  which comprise one sugar fatty acid ester in combination with one plant extract (either an extract of *Waltheria indica* or an extract of *Pisum sativum*);
  which comprise one sugar fatty acid ester in combination with both plant extracts, which comprise a mixture of more than one sugar fatty acid ester in combination with one plant extract (either an extract of *Waltheria indica* or an extract of *Pisum sativum*);

which comprise a mixture of more than one sugar fatty acid ester in combination with both plant extracts.

Component (a) Sugar Fatty Acid Ester

The skin whitening active according to the invention comprises at least on sugar fatty acid ester.

The terms "sugar fatty acid esters" and "sugar esters" are used synonymously throughout the invention.

Sugar esters are known non-ionic surfactants which may be obtained by the relevant methods of preparative organic chemistry, for example by reaction of fatty acid methyl esters with corresponding sugars or enzymatically, as described for example in International patent application WO99/02722 (Laboratoires Sérobiologiques). Sugar esters with different glycoside and acyl components and different degrees of esterification are commercially obtainable, for example from the Cognis, Sisterna or and Mitsubishi-Kagaku Foods Corporation. Typical examples of suitable sugar esters are shown below:

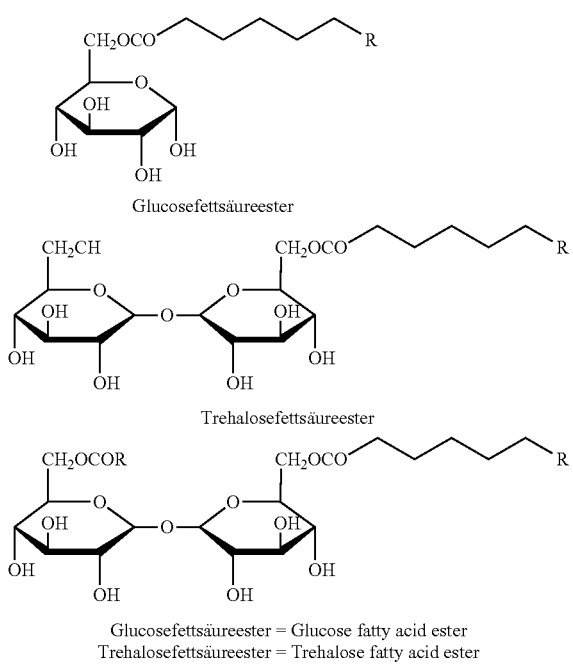

Glucosefettsäureester = Glucose fatty acid ester
Trehalosefettsäureester = Trehalose fatty acid ester Basically, sugar esters derived from mono-, di- and/or oligosaccharides are suitable, including aldohexoses (for example glucose, methylglucose, mannose, galactose); deoxyaldoses (for example rhamnose, fucose, deoxyribose); aldopentoses (for example ribose, arabinose, xylose); ketoses (for example fructose in pyranosyl or furanosyl form); disaccharides (for example trehalose, sucrose, maltose, isomaltose, cellobiose, melibiose, gentobiose, lactose) and tri-, tetra-, penta- and oligosaccharides.

In a preferred embodiment sugar esters derived from mono- and/or disaccharides are preferred.

Fructose, glucose, trehalose, saccharose and/or sucrose esters are preferred, sucrose (=saccharose) esters being particularly preferred.

The acyl component of the esters may be derived from fatty acids corresponding to formula (I):

$$R_1CO\text{—}OH \qquad (I)$$

in which $R_1$—CO is a linear or branched, saturated or unsaturated acyl or hydroxyacyl group containing 6 to 22 and preferably 7 to 18, more preferably 8 to 16, more preferably 10 to 16 carbon atoms, more preferably 10 to 14 carbons atoms. In a preferred embodiment the acyl component of the ester has 0 and/or 1 to 3 double bonds.

In a preferred embodiment the acyl group of the sugar ester is derived from saturated fatty acids.

Typical examples are sugar esters of caproic acid, 2-hydroxycaproic acid, 6-hydroxycaproic acid, caprylic acid, 2-ethylhexanoic acid, capric acid, 10-hydroxycaproic acid, lauric acid, 12-hydroxylauric acid, isotridecanoic acid, myristic acid, palmitic acid, palmitoleic acid, 16-hydroxypalmitic acid, stearic acid, isostearic acid, oleic acid, elaidic acid, petroselic acid, linoleic acid, linolenic acid, conjugated linoleic acid, elaeostearic acid, 12-hydroxystearic acid, ricinoleic acid, arachidonic acid, gadoleic acid, behenic acid and erucic acid and technical mixtures thereof. The sugar esters may also be derived from dicarboxylic acids containing 2, preferably 4 to 22 and preferably 6 to 18 carbon atoms, such as for example adipic acid, azelaic acid, decanedicarboxylic acid, dodecanedicarboxylic acid, tetradecanedicarboxylic acid, hexadecanedicarboxylic acid, octadecanedicarboxylic acid, octadecenedicarboxylic acid, and technical mixtures thereof.

In a preferred embodiment the acyl component of the sugar ester is derived from the group consisting of capric acid, lauric acid or myristic acid.

The esters may contain 1 to 8 ester groups according to the hydroxyl groups available. However, products with an average degree of esterification of 1 to 6 and, more particularly, 1 to 4, especially 1.5 to 2.5 are preferably used.

In a preferred embodiment of the invention sugar fatty acid esters are used, wherein the sugar component is selected from glucose, fructose, sucrose, or trehalose and the acyl component is selected from linear or branched, saturated or unsaturated acyl or hydroxyacyl group containing 10 to 14 carbon atoms. Preferably these sugar esters have an average degree of esterification of 1 to 4.

In a preferred embodiment of the invention sugar fatty acid esters are used, wherein the sugar component is selected from glucose, fructose, sucrose, or trehalose and the acyl component is selected from capric acid, lauric acid or myristic acid. Preferably these sugar esters have an average degree of esterification of 1 to 4.

The skin-whitening active according to the invention can comprise one or more sugar fatty acid esters.

Component (b-1): Extracts from *Waltheria indica*

In one embodiment of the invention, the skin-whitening active according to the invention comprises at least one extract of *Waltheria indica* (component b-1).

The plant *Waltheria indica* (alternative botanical names are *Waltheria americana, Waltheria pyrolaefolia, Waltheria makinoi* Hayata) belongs to the family of Sterculiaceae. It is a small shrub 2 to 6 feet tall with velvety hairs covering all parts of the plant. The oblong to oval leaves are up to 6 inches long and 2 inches wide with toothed edges and conspicuous veins. The fragrant yellow flowers grow in small, dense clusters in the leaf axils.

Generally any and all parts of the *Waltheria indica* plant can be used to prepare an extract according to the invention. Fresh plants or plant parts may be used as the starting material although dried plants and/or plant parts—which may be mechanically size-reduced before extraction—are normally used. Entire plants, plant parts or seeds, fresh or dried, may be used as starting material, which can be mechanically size-reduced. Preferably dried plants and/or plant parts—which may be mechanically size-reduced before extraction—are used. In a preferred embodiment leaves and/or buds are used.

Component (b-2): Extracts from *Pisum sativum*

*Pisum sativum* is a plant of the family of the Fabaceae/Leguminosaea, belonging to the sub-family of Faboideae.

Common varieties belonging to the genus of *Pisum sativum* include *Pisum sativum* L. convar. *Sativum, Pisum sativum* L. convar. *medullare Pisum sativum* L. convar. *Axiphium. Pisum granda sneida* L. convar. *sneidulo* p. *shneiderium*

Generally any and all parts of the *Pisum sativum* plant can be used to prepare an extract according to the invention. Fresh plants or plant parts, preferably the seeds ("peas") may be used as the starting material although dried plants and/or plant parts—which may be mechanically size-reduced before extraction—are normally used. Entire plants, plant parts or seeds, fresh or dried, may be used as starting material, which can be mechanically size-reduced. Preferably dried plants and/or plant parts—which may be mechanically size-reduced before extraction—are used. In a preferred embodiment only the seeds ("peas") are used.

Preparation of the Extracts (b-1) and/or (b-2)

Component (b-1) as well as component (b-2) according to the invention may be prepared by known methods of extracting plants or parts thereof. In the interests of simplicity, particulars of suitable conventional extraction processes, such as maceration, re-maceration, digestion, agitation maceration, vortex extraction, ultrasonic extraction, countercurrent extraction, percolation, re-percolation, evacolation (extraction under reduced pressure), diacolation and solid/liquid extraction under continuous reflux in a Soxhlet extractor, which are familiar to the expert and which may all be used in principle, can be found for example in Hagers Handbuch der pharmazeutischen Praxis (5th Edition, Vol. 2, pp. 1026-1030, Springer Verlag, Berlin-Heidelberg-New York 1991). Suitable solvents for the extraction process are organic solvents, water, preferably distilled hot water with a temperature above 80° C. and, in particular, between 85 and 90° C. or mixtures of organic solvents and water, more particularly low molecular weight alcohols with more or less large water contents. Extraction with methanol, ethanol, pentane, hexane, heptane, acetone, ethyl methyl ketone, propylene glycols, butylenes glycols, polyethylene glycols and ethyl acetate, mixtures thereof and water-containing mixtures thereof is particularly preferred. In a preferred embodiment the extract is obtained by extraction with a solvent selected from the group consisting of water, butylene glycol, pentylene glycol and mixture thereof. In a preferred embodiment the extract is obtained by extraction with water.

The extraction process is generally carried out at 4 to 100° C., preferably at 20 to 90° C., more preferably at 30 to 90° C., and more particularly at the boiling temperature of the alcohol or the water/alcohol mixture. In one preferred embodiment, the extraction process is carried out in an inert gas atmosphere to avoid oxidation of the active principles of the extract. This is particularly important where extraction is carried out at temperatures above 40° C. The extraction process is generally conducted at pH from 2.5 to 11; preferably from 4 to 9. The extraction times are selected by the expert in dependence upon the starting material, the extraction process, the solvent, the extraction temperature, the pH conditions and the ratio of solvent to raw material, etc.

After the extraction process, the crude extracts obtained may optionally be subjected to other typical steps, such as for example purification, concentration and/or de-coloration.

If desired, the extracts thus prepared may be subjected, for example, to the selective removal of individual unwanted ingredients. The extraction process may be carried out to any degree, but is usually continued to exhaustion. Typical further purification steps are using membrane separation techniques such as nanofiltration, ultrafiltration, precipitation techniques, adsorption/desorption techniques on resins, chromatography techniques. Typical yields (=extract dry matter, based on the quantity of raw material used) in the extraction of press residues are in the range from 0.5 to 10 and more particularly 1 to 5% by weight. The present invention includes the observation that the extraction conditions and the yields of the final extracts may be selected by the expert according to the desired application. If desired, the extracts may then be subjected, for example, to spray drying or freeze drying.

If desired the extracts can be mixed with one or more auxiliaries, such as e.g. mannitol, sorbitol, maltodextrine, cyclodextrine, glycerine, sugars as saccharose, fructose, glucose or trehalose.

Skin-Whitening Active

In one embodiment of the invention the skin-whitening active comprises at least 10 weight-% by weight of (a), (b-1) and/or (b-2), and in a preferred embodiment at least 20% of (a), (b-1) and/or (b-2).

The skin-whitening active according to the invention can comprise other components. In one embodiment of the invention, the skin-whitening active comprises at least one further component selected from the group consisting of auxiliaries, additives, solubilizers or mixtures thereof.

In one embodiment of the invention the skin-whitening active further comprises at least one an auxiliary.

In one embodiment of the invention the skin-whitening active further comprises at least one an auxiliary selected from the group consisting of mannitol, sorbitol, maltodextrine, cyclodextrine, glycerine, sugars as saccharose, fructose, glucose or trehalose.

In one embodiment of the invention the skin-whitening active further comprises at least one solubilizer.

In one embodiment of the invention the skin-whitening active further comprises at least one solubilizer selected from the group consisting of polyethylene glycol ethers of coconut oil, polyethylene and polypropylene glycol ethers of lauric acid, polyethylene glycol derivatives of hydrogenated castor oil, polyethylene glycol ethers of glyceryl stearate, polyethylene glycol ethers of cetearyl alcohol, sodium cetearyl sulphate, esters of sorbitol and sorbitol anhydrides with long chain fatty acids condensed with ethylene oxide or mixtures thereof.

In a preferred embodiment of the invention the skin-whitening active further comprises at least one an auxiliary and at least one solubilizer.

The skin-whitening active according to the invention can be prepared by simply mixing components (a), (b-1) and/or (b-2), optionally with further components.

In one embodiment the plant extract (components b-1 and/or b-2) can be solubilized/dissolved, optionally under heating and the sugar fatty acid ester can then be added. Preferably the sugar fatty acid ester is solubilized before being added to component (a).

The solubilization of the sugar fatty acid ester can be conducted under elevated temperatures. Any known suitable solubilizers can be used for the sugar fatty acid esters, such as e.g. coceth-7 [Coceth-7 is the polyethylene glycol ether of Coconut Alcohol (q.v.) that conforms to the general formula R—(OCH2CH2)$_n$-OH, wherein R represents the fatty alcohols derived from *Cocos Nucifera* (Coconut) Oil (q.v.) and n has an average value of 7], PPG-1-PEG-9 lauryl glycol ether, PEG-40 hydrogenated castor oil [PEG-40 Hydrogenated Castor Oil is a polyethylene glycol derivative of Hydrogenated Castor Oil (q.v.) with an average of 40 moles of ethylene oxid], PEG-20 glyceryl stearate, PEG-20 [Glyceryl Stearate is the polyethylene glycol ether of Glyceryl Stearate (q.v.) that conforms generally to the following formula, where x+y+z has an average value of 20].

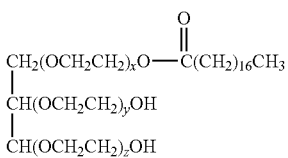

Ceteareth-12 [Ceteareth-12 is the polyethylene glycol ether of Cetearyl Alcohol (q.v.) that conforms generally to the formula R—(OCH2CH2)$_n$-OH wherein R represents a blend of alkyl groups derived from cetyl and stearyl alcohol and n has an average value of 12], sodium cetearyl sulphate, or polysorbates (esters of sorbitol and sorbitol anhydrides with long chain fatty acids and condensed with ethylene oxide), such as e.g. Polysorbate-20 (Laurate Esters, approx. 20 moles EO) or Polysorbate-80 (Oleate esters, approx 80 moles EO), or mixtures thereof.

The ratio between component (a) [the sugar fatty acid ester] and components (b-1) and/or (b-2) [the plant extract(s)] is preferably between 100:1 and 1:100, and more preferentially between 50:1 and 1:50 (based on a dry weight basis).

In a preferred embodiment the ratio between component (a) [the sugar fatty acid ester] and components (b-1) and/or (b-2) [the plant extract(s)] is between 50:1 and 1:1, preferably 40:1 to 1:1, more preferably between 30:1 and 1:1, between 25:1 and 1:1 and between 15:1 and 1:1 (based on a dry weight basis).

The skin-whitening active according to the invention is preferably used in cosmetic compositions. One preferred cosmetic use is as a skin-whitener. One preferred cosmetic use is as inhibitor of melanogenesis. The skin-whitening active according to the invention is preferably used as an agent to decrease tyrosinase activity in melanocytes and as an agent to decrease melanosome maturation in melanocytes.

Cosmetic Compositions

The invention is further directed to cosmetic compositions comprising the skin-whitening active according to the invention. These cosmetic compositions preferably contain the skin-whitening active in a concentration between 0.01 and 10% and more preferentially between 0.1 and 5% by weight based on the cosmetic composition.

Further Skin-Whitening Agent (c)

In one embodiment of the invention the cosmetic composition comprising the skin-whitening active, comprise at least one further skin-whitening agent (c).

The further skin-whitening agent can be chosen from any known skin-whitening agent, e.g. kojic acid, hydroquinone, alpha- and beta-arbutin, other hydroquinone glycosides, deoxyarbutin, ferulic acid, diacetyl-boldine, azelaic acid, octadecenedioic acid, linoleic acid, conjugated linoleic acid, alpha-lipoic acid, glutathione and derivatives, undecylenoyl-phenylalanine, vitamin C and derivatives as magnesium L-ascorbyl-phosphate, niacinamide, 4-n-butyl-resorcinol, alpha- and beta-hydroxy acids, ellagic acid, resveratrol, *Morus alba* extracts, glabridin and liquorice extracts, imperatorin and isoimperatorin and *Angelica dahurica* extracts, centaureidin and Yarrow extracts, *Bellis perennis* extracts, *Phyllanthus emblica* extracts, water cress extracts, *Veratum nigrum* extracts, *Sophora flavescens* extracts, ascomycete-derived melanin-degrading enzyme.

In one embodiment of the invention the further skin-whitening agent is at least one plant extract.

In one embodiment of the invention the further skin-whitening agent is selected from the group consisting of kojic acid, alpha- and beta-arbutin, other hydroquinone glycosides, deoxyarbutin, ferulic acid, conjugated linoleic acid, vitamin C and derivatives as magnesium L-ascorbyl-phosphate, niacinamide and/or liquorice extracts.

The cosmetic composition according to the invention is preferably used as a skin-whitener. The cosmetic composition according to the invention is preferably used as an inhibitor of melanogenesis. The cosmetic composition according to the invention is preferably used to decrease tyrosinase activity in melanocytes and to decrease melanosome maturation in melanocytes.

The cosmetic compositions according to the invention can for example be in the form of a hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, hydrotropes, solubilizers, preservatives, perfume oils, dyes and the like.

In one embodiment of the invention the cosmetic composition further comprises at least one surfactant.

Surface-active substances which may be present are anionic, nonionic, cationic and/or amphoteric or zwitterionic surfactants, the content of which in the compositions is usually about 1 to 70% by weight, preferably 5 to 50% by weight and in particular 10 to 30% by weight. Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants comprise polyglycol ether chains, these can have a conventional homologue distribution, but preferably have a narrowed homologue distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these can have a conventional homologue distribution, but preferably have a narrowed homologue distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds. Typical examples of particularly suitable mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

In one embodiment of the invention the cosmetic composition further comprises at least one oil body.

Suitable oil bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes.

In one embodiment of the invention the cosmetic composition further comprises at least one emulsifier.

Suitable emulsifiers are, for example, nonionogenic surfactants from at least one of the following groups:

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogues thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. $C_{12/18}$-fatty acid mono- and diesters of addition products of ethylene oxide to glycerol are known as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxy-stearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxy-ethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —SO$_3$H group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionic, cocoacylaminoethylaminopropionate and $C_{12/18}$-acyl-sarcosine. Finally, cationic surfactants are also suitable as emulsifiers, those of the ester quat type, preferably methyl-quaternized difatty acid triethanolamine ester salts, being particularly preferred.

In one embodiment of the invention the cosmetic composition further comprises at least one fat or wax.

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

In one embodiment of the invention the cosmetic composition further comprises at least one pearlescent wax.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

In one embodiment of the invention the cosmetic composition further comprises at least one consistency regulator and/or thickener.

Suitable consistency regulators are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

In one embodiment of the invention the cosmetic composition further comprises at least one superfatting agent.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

In one embodiment of the invention the cosmetic composition further comprises at least one stabilizer.

Stabilizers which can be used are metal salts of fatty acids, such as, for example, magnesium, aluminium and/or zinc stearate or ricinoleate.

In one embodiment of the invention the cosmetic composition further comprises at least one polymer.

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryidimonium hydroxypropyl hydrolyzed collagen (Lamequat®L/Grünau), quaternized wheat polypeptides, polyethyleneimine, cationic silicone polymers, such as, for example, amodimethicones, copolymers of adipic acid and dimethylaminohydroxy-propyldiethylenetriamine (Cartaretins®/Sandoz), copolymers of acrylic acid with dimethyldiallylammonium chloride (Merquat® 550/ Chemviron), polyaminopolyamides, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylamino-ethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

In one embodiment of the invention the cosmetic composition further comprises at least one silicone compound.

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

In one embodiment of the invention the cosmetic composition further comprises at least one UV photoprotective filter.

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzalmalonate;

triazine derivatives, such as, for example, 2,4,6-trianilino (p-carbo-2'-ethyl-1'-hexyloxy)-1,3,5-triazine and octyltriazone or dioctylbutamidotriazone (Uvasorb® HEB);

propane-1,3-diones, such as, for example, 1-(4-tert-butylphenyl)-3-(4'-methoxyphenyl)propane-1,3-dione;

ketotricyclo(5.2.1.0)decane derivatives.

Suitable water-soluble substances are:

2-phenylbenzimidazole-5-sulphonic acid and the alkali metal, alkaline earth metal, ammonium, alkylammonium, alkanolammonium and glucammonium salts thereof;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)benzenesulphonic acid and 2-methyl-5-(2-oxo-3-bornylidene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds. The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

In one embodiment of the invention the cosmetic composition further comprises at least one biogenic active ingredient and/or antioxidant.

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), auro-thioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

In one embodiment of the invention the cosmetic composition further comprises at least one anti-microbial agent and/or preservative.

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

In one embodiment of the invention the cosmetic composition further comprises at least one film former.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

In one embodiment of the invention the cosmetic composition further comprises at least one swelling agent.

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

In one embodiment of the invention the cosmetic composition further comprises at least one hydrotropic agent.

To improve the flow behaviour, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are glycerol;
alkylene glycols, such as, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, such as, for example, technical-grade diglycerol mixtures with a diglycerol content of from 40 to 50% by weight;
methylol compounds, such as, in particular, trimethylolethane, trimethylolpropane, trimethylolbutane, pentaerythritol and dipentaerythritol;
lower alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcohol amines, such as diethanolamine or 2-amino-1, 3-propanediol.

The total amount of further components can be 1 to 50% by weight, preferably 5 to 40% by weight, based on the compositions. The compositions can be prepared by customary cold or hot processes; preference is given to using the phase-inversion temperature method.

EXAMPLES

Example 1: Extract of *Waltheria indica*

1.2 kg *Waltheria indica* leaves were added to 20 liters of distilled water, then heated to 85-90° C. and stirred for 2 hours. The extract was then cooled to room temperature and centrifuged for 15 min at 3500 g. The brown extract obtained was then hydrolysed for 4 hours at 60° C. with papain, a proteinase from papayas. The enzyme was deactivated by heat shock at 90° C. The extract was then cooled to room temperature, and after addition of PVP (polyvinyl pyrrolidone), was separated from the residue by filtration through depth filters with a mean porosity of 200 to 400 nm (from Seitz, Bordeaux, France), an extract with a dry residue of 1.2% by weight was obtained. The extract was spray-dried at a starting temperature of 185° C. and an end temperature of 80° C., after the addition of mannitol as an auxiliary in the proportion of 10:90 by weight respectively for the extracted material: mannitol.

The same treatment produced an extract of a dry residue of 1 to 10 weight % depending on the starting material.

Example 2: Extract of *Waltheria indica*

1.2 kg *Waltheria indica* leaves were added to 5.5 liters of distilled water and 13.2 kg pentylene glycol heated to 85-90° C. and stirred for 2 hours. The extract was then cooled to room temperature and centrifuged for 15 min at 3500 g. The brown extract was separated from the residue by filtration through depth filters with a mean porosity of 200 to 400 nm (from Seitz, Bordeaux, France), an extract with a dry residue of 1.7% by weight obtained.

Example 3A: Extract of *Waltheria indica*

2 kg *Waltheria indica* leaves were percolated for 2 hours with 30 liters distilled water heated to 90° C. The extract thus obtained was cooled to room temperature and, after addition of PVP (polyvinyl pyrrolidone), was separated from the residue by filtration through depth filters with a mean porosity of 200 to 400 nm (from Seitz, Bordeaux, France), an extract with a dry residue of 0.5% by weight being obtained. The same treatment produced a dry residue of 0.5 to 5% by weight depending on the starting material. The extract was spray-dried at a starting temperature of 185° C. and an end temperature of 80° C., optionally after the addition of an auxiliary, such as mannitol (½ auxiliary, ½ extracted material or ⅒ auxiliary and ⁹⁄₁₀ extracted material).

Example 3B: Preparation of Water/Alcohol Extract of *Waltheria Indica*

To prepare a water/alcohol extract, the following steps were carried out: 200 g of the size-reduced plant material were suspended in 2 liters 70% by weight aqueous ethanol in a reaction vessel; extraction was conducted under reflux for 1 hour with stirring; then filtration was conducted in a Buchner filter equipped with fine filters; then the supernatant was collected, followed by a concentration of the ethanol phase by evaporation under reduced pressure, and centrifuging for 10 min. at 5000 G to remove insolubles and subsequent filtration; obtained yield by weight was 14.6%. Water was removed from the extract by direct spraying of the plant extract, optionally after addition of an auxiliary, such as maltodextrin ([⅔] auxiliary, [⅓] extracted material).

Example 4: Extract of *Pisum sativum*

9.5 kg of *Pisum sativum* seeds were grinded to obtain a powder, and were added to 6.5 liters of distilled water. After addition of $H_2SO_4$ to reach pH 5, the mixture was heated to 45-50° C. and stirred for 2 hours. The extract was then cooled to room temperature, centrifuged to separate the solids and filtered through 0.65 μm filters to obtain a clear liquid. The extract was then concentrated around 2.5-3 times by tangential ultrafiltration with 5000 Da membranes, and then diafiltered around 2 times to obtain 1.2 liters of an extract with a dry residue of 4.3% by weight. The extract was spray-dried at a starting temperature of 190° C. and an end temperature of 120° C.

Example 5: Sucrose Fatty Acid Esters

Sucrose laurate, commercialized under SURFHOPE® SE COSME C-1205, was supplied by Mitsubishi-Kagaku Foods Corporation.

Example 6: Mix Sucrose Fatty Esters-Extract of *Waltheria indica*

10.6 kg *Waltheria indica* extract of example 2, and 16 kg pentylene glycol, were heated to 70° C. 6.6 kg of Sucrose fatty ester was then added in this solution and solubilized with turax. The product was then cooled to room temperature.

Example 7: Mix Sucrose Fatty Ester-Extract of *Pisum sativum*

0.48 kg extract of *Pisum sativum* of example 4 was solubilized in 10.7 liters distilled water 0.5 kg of sucrose fatty acid esters were solubilized under mixer at 70° C. in 12.5 liters distilled water and 3.75 kg solubilizer. The product was cooled to room temperature and the solution of *Pisum sativum* extract was added under mixer.

Example 8: Melanogenesis Inhibition Assay

Melanocytes (B16 cell line) were inoculated in standard medium of cell culture with foetal calf serum (FCS). After an incubation for 3 days at 37° C. and $CO_2$=5%, growth medium was exchanged for standard medium with a range of concentrations for each ingredient to be tested and a control without ingredient. After an incubation of 3 days, the level of melanin is measured by recording the optical density at 475 nm. After washing the cells by a balanced salt, and homogenisation in a solution of 0.1 M NaOH, the number of viable cells is determined by evaluation of the level of cellular proteins (Bradford's method).

Combinations of ingredients have been tested on the same cell cultures, in parallel with the ingredients alone. The results are expressed in % against control (cell culture medium without ingredient) as a mean+/−SEM (Standard Error of Mean) on 2 or 3 assays, each in triplicate.

Example 8-1: Combination of Sucrose Laurate and *Waltheria indica* Extract

The extract according to example 1 and the sucrose laurate according to example 5 were tested:

TABLE 1

Rate of cellular proteins in %/control (mean +/− SEM on 3 assays in triplicate):

| | | *Waltheria indica* extract of example 1 Dose % (w/v) | | | |
|---|---|---|---|---|---|
| | | Control | 0.03 | 0.1 | 0.3 |
| Sucrose laurate of example 5 Dose % (w/v) | Control | 100 +/− 0 | 101 +/− 1 | 97 +/− 2 | 96 +/− 3 |
| | 0.0003 | 102 +/− 4 | nt | 99 +/− 4 | 95 +/− 7 |
| | 0.001 | 99 +/− 3 | 100 +/− 3 | 102 +/− 2 | 97 +/− 5 | nt: not tested

The results demonstrated that the sucrose laurate, the *Waltheria indica* extract and their combination have not modified the rate of viable B16 melanocytes.

TABLE 2

Rate of melanin in %/control (mean +/− SEM on 3 assays in triplicate):

| | | *Waltheria indica* extract of example 1 Dose % (w/v) | | | |
|---|---|---|---|---|---|
| | | Control | 0.03 | 0.1 | 0.3 |
| Sucrose laurate of example 5 Dose % (w/v) | Control | 100 +/− 0 | 67 +/− 20 | 56 +/− 16 | 34 +/− 9 |
| | 0.0003 | 56 +/− 18 | nt | 44 +/− 11 | 30 +/− 10 |
| | 0.001 | 54 +/− 16 | 49 +/− 12 | 39 +/− 7 | 28 +/− 6 | nt: not tested

Table 2 shows that with the sugar fatty acid ester alone at a concentration of 0.0003% the rate of melanin can be reduced to 56+/−18%. Increasing the concentration of the sugar fatty acid ester by 3 fold (to 0.001%) does not lead to a significant increase in melanin reduction (rate of melanin 54+/−16% at a concentration of 0.001% sucrose laurate).

A significant further reduction of melanin synthesis can only be achieved by adding an extract of *Waltheria indica*: by adding 0.3% a reduction to a melanin rate of 28+/−6% can be achieved.

TABLE 3

Ratio of rate of cellular proteins on rate of melanin (mean on 3 assays in triplicate)

| | | *Waltheria indica* extract of example 1 Dose % (w/v) | | | |
|---|---|---|---|---|---|
| | | Control | 0.03 | 0.1 | 0.3 |
| Sucrose laurate of example 5 Dose % (w/v) | Control | 1.0 | 1.5 | 1.7 | 2.8 |
| | 0.0003 | 1.8 | nt | 2.3 | nt |
| | 0.001 | 1.8 | 2.0 | 2.6 | 3.5 | nt: not tested

The results in Tables 2 and 3 shows that the combination of sucrose laurate and *Waltheria indica* extract, for different ratios, have an improved effect on melanogenesis inhibition which is superior to each product alone at similar concentration.

Example 8-2: Combination of Sucrose Laurate and *Pisum sativum* Extract

TABLE 4

Rate of cellular proteins in %/control
(mean +/− SEM on 2 assays in triplicate):

|  |  | *Pisum sativum* extract of example 4 Dose % (w/v) | |
| --- | --- | --- | --- |
|  |  | Control | 0.03 |
| Sucrose laurate of example 5 Dose % (w/v) | Control 0.001 | 100 +/− 0 90 +/− 9 | 106 +/− 1 95 +/− 1 |

The results demonstrated that the sucrose laurate, the *Pisum sativum* extract and their combination have not modified the rate of viable B16 melanocytes.

TABLE 5

Rate of melanin in %/control (mean +/− SEM on 2 assays in triplicate):

|  |  | *Pisum sativum* extract of example 4 Dose % (w/v) | |
| --- | --- | --- | --- |
|  |  | Control | 0.03 |
| Sucrose laurate of example 5 Dose % (w/v) | Control 0.001 | 100 +/− 0 56 +/− 7 | 56 +/− 1 39 +/− 3 |

TABLE 6

Ratio of rate of cellular proteins on rate of melanin
(mean on 2 assays in triplicate)

|  |  | *Pisum sativum* extract of example 4 Dose % (w/v) | |
| --- | --- | --- | --- |
|  |  | Control | 0.03 |
| Sucrose laurate of example 5 Dose % (w/v) | Control 0.001 | 1.0 1.6 | 1.9 2.4 |

The results in Tables 5 and 6 shows that the combination of sucrose laurate and *Pisum sativum* extract have an improved effect on melanogenesis inhibition which is superior to each product alone at similar concentration.

Example 9 Tyrosinase Activity on Melanocytes

Melanocytes (B16 cell line) were inoculated in standard medium of cell culture with foetal calf serum (FCS). After an incubation for 3 days at 37° C. and $CO_2$=5%, growth medium was exchanged for standard medium with a range of concentrations for each ingredient to be tested and a control without ingredient. Combinations of ingredients have been tested on the same cultures, in parallel with ingredients alone. After an incubation of 3 days, B16 melanocytes were incubated with a solution of DL-DOPA at 0.1% during 2 hours at 37° C. The activity of Tyrosinase was evaluated by recording at 2 hours, the optical density at 475 nm of the DL-DOPA solution. The optical density at 475 nm is expressed as a % against control and presented as a mean+/−SEM (standard error of mean) of triplicates.

In parallel, a second set of cultures of B16 melanocytes treated in the same manner as for tyrosinase activity measurement was used to determine the cell number by measuring the quantity of proteins in attached cells. By this way, it was possible to evaluate the harmlessness of the products at the used dose.

TABLE 7

Tyrosinase activity in %/control (mean +/− SEM on triplicates):

|  |  | *Waltheria indica* extract of example 1 Dose % (w/v) | | |
| --- | --- | --- | --- | --- |
|  |  | Control | 0.001 | 0.002 |
| Sucrose laurate of example 5 Dose % (w/v) | Control 0.005 0.01 | 100 +/− 14 75 +/− 6 64 +/− 7 | 99 +/− 2 69 +/− 10 nt | 96 +/− 5 nt 53 +/− 6 | nt: not tested
Reference with kojic acid 0.03%: tyrosinase activity of 83% +/− 5 vs control Only sucrose laurate decreases the tyrosinase activity, whereas *Waltheria indica* extract has no efficacy. When associated at the same dose, the combination of sucrose laurate and *Waltheria indica* extract gives an efficacy higher than sucrose laurate alone, demonstrating a synergistic effect.

TABLE 7bis

Amount of cellular proteins in %/control (mean +/− SEM on triplicates):

|  |  | *Waltheria indica* extract of example 1 Dose % (w/v) | | |
| --- | --- | --- | --- | --- |
|  |  | Control | 0.001 | 0.002 |
| Sucrose laurate of example 5 Dose % (w/v) | Control 0.005 0.01 | 100 +/− 3 87 +/− 6 86 +/− 7 | 98 +/− 3 89 +/− 2 nt | 100 +/− 7 nt 88 +/− 7 | nt: not tested
Reference with kojic acid 0.03%: amount of cellular proteins of 115% +/− 4 vs control Sucrose laurate as well as *Waltheria indica* extract tested separately or mixed, have not distinctly decreased the amount of cellular proteins and therefore they do not show any toxic effects at these concentrations.

TABLE 8

Tyrosinase activity in %/control (mean +/− SEM on triplicates):

|  |  | *Pisum sativum* extract of example 4 Dose % (w/v) | | |
| --- | --- | --- | --- | --- |
|  |  | Control | 0.0005 | 0.001 |
| Sucrose laurate of example 5 Dose % (w/v) | Control 0.005 0.01 | 100 +/− 14 75 +/− 6 64 +/− 7 | 104 +/− 4 70 +/− 6 nt | 104 +/− 12 nt 43 +/− 2 | nt: not tested
Reference with kojic acid 0.03%: tyrosinase activity of 83% +/− 5 vs control Only sucrose laurate decreases the tyrosinase activity, whereas *Pisum sativum* extract has no efficacy. When associated at the same dose, the combination of sucrose laurate and *Pisum sativum* extract gives an efficacy higher than sucrose laurate alone, demonstrating a synergistic effect.

TABLE 8bis

Amount of cellular proteins in %/control (mean +/− SEM on triplicates):

|  |  | Pisum sativum extract of example 4 Dose % (w/v) | | |
|---|---|---|---|---|
|  |  | Control | 0.0005 | 0.001 |
| Sucrose laurate of example 5 Dose % (w/v) | Control | 100 +/− 3 | 96 +/− 5 | 109 +/− 6 |
|  | 0.005 | 87 +/− 6 | 101 +/− 2 | nt |
|  | 0.01 | 86 +/− 7 | nt | 90 +/− 9 | nt: not tested

Reference with kojic acid 0.03%: amount of cellular proteins of 115% +/− 4 vs control Sucrose laurate as well as *Pisum sativum* extract tested separately or mixed, have not distinctly decreased the amount of cellular proteins and therefore they do not show any toxic effects at these concentrations.

Example 10: Whitening Efficacy In-Vivo on Asian Volunteers

The test was conducted under dermatological control on 26 Asian skin type aged from 18 to 45 years, with dark or very dark-skin particularly on the external side of the forearm. An emulsion A containing 0.5% of sucrose laurate and 0.05% of *Pisum sativum* extract was tested in comparison with an emulsion B containing 2% hydroquinone (See Table 9) and a non-treated control. The emulsions were applied twice daily during 6 weeks; in a dose of 5 mg/cm² on two test sites on the forearms. The quantitative evaluation of whitening efficiency was done by skin color measurement (Pigmentation Index) using the Mexameter M16 (Courage and Khazaka, Germany) before treatment and after 6 weeks of treatment. The results are expressed as % of decrease of Pigmentation Index vs before treatment and presented as a mean+/−SEM (standard error of mean) (table 10).

TABLE 9

Emulsion Compositions

| Components (INCI) | Emulsion A | Emulsion B |
|---|---|---|
| Glyceryl Stearate (and) Ceteareth-20 (and) Ceteareth-12 (and) Cetearyl Alcohol (and) Cetyl Palmitate | 6.00 | 6.00 |
| Cetearyl Alcohol | 1.80 | 1.80 |
| Octyl Palmitate | 5.00 | 5.00 |
| Capric Caprylic Triglycerides | 4.00 | 4.00 |
| Dicaprylyl Carbonate | 4.00 | 4.00 |
| Octyldodecanol | 2.00 | 2.00 |
| Dimethicone | 0.50 | 0.50 |
| Triclosan and Ethylparaben (Elestab 4121) | 0.30 | 0.30 |
| Chlorphenesin and Methylparaben (Elestab 50J) | 0.40 | 0.40 |
| Xanthan Gum | 0.20 | 0.20 |
| Glycerin | 2.30 | 3.00 |
| Sodium Hydroxide 10% | 0.40 | 0.40 |
| Carbomer | 0.20 | 0.20 |
| Hydroquinone | — | 2.00 |
| Complex containing 20% Sucrose laurate (according to example 5), 2% *Pisum sativum* extract (according to example 4) and 28% of Glycerin | 2.50 | — |
| Water | Qsf 100 | Qsf 100 |

TABLE 10

Study of the whitening efficacy in vivo on 26 Asian dark skin type panellists. Evolution after 6 weeks of treatment in comparison with before treatment. Quantitative measurement by colorimetry (Mexameter ®).

| Mean ± SEM | Control | Emulsion B containing 2% hydroquinone | Emulsion A containing 0.5% Sucrose laurate and 0.05% *Pisum sativum* extract |
|---|---|---|---|
| Week 0 (mexameter value) | 331.9 ± 22.30 | 331.3 ± 22 | 343.7 ± 21.4 |
| Week 6 (mexameter value) | 332.7 ± 22.2 | 304.9 ± 15.8 | 319.1 ± 19.8 |
| (Week 6 − Week 0)/ Week 0 (%) | 0.30 ± 0.16 | −6.1 ± 1.9 (*) | −6.9 ± 1.5 (**) |

Statistics: Mean ± SEM on 26 volunteers
Student's t test
(*) p = 0.0019
(**) p < 0.0001

The Mexameter results indicated a significant decrease in the degree of pigmentation during and after using the tested emulsions in comparison to the control zone without treatment. This whitening activity corresponds to the diminution of Mexameter values.

The treatment of dark Asian skin with emulsion containing the combination of sucrose laurate and *Pisum sativum* extract induced a significant whitening efficacy already after 6 weeks of treatment, similar to the benchmark hydroquinone, without any skin irritation.

The invention claimed is:

1. A skin whitening agent comprising:
   (a) one or more sucrose esters of lauric acid; and
   (b) an extract of *Pisum sativum* obtained with water heated at 45-50° C.;
   wherein the ratio of the sucrose esters of lauric acid to the extract is 10:1 based on a dry weight basis and the extract is present in an amount effective to increase the tyrosinase inhibiting efficacy of the sucrose esters of lauric acid.

2. The skin whitening agent of claim 1 which comprises at least 0.001% w/w *Pisum sativum* extract.

3. The skin whitening agent of claim 1, further comprising a component selected from the group consisting of auxiliaries, additives, solubilizers and mixtures thereof.

4. The skin whitening agent of claim 3, wherein the auxiliary is selected from the group consisting of mannitol, sorbitol, maltodextrine, cyclodextrine, glycerine, and sugars.

5. The skin whitening agent of claim 3, wherein the solubilizer is selected from the group consisting of polyethylene glycol ethers of coconut oil, polyethylene and polypropylene glycol ethers of lauric acid, polyethylene glycol derivatives of hydrogenated castor oil, polyethylene glycol ethers of glyceryl stearate, polyethylene glycol ethers of cetearyl alcohol, sodium cetearyl sulphate, esters of sorbitol and sorbitol anhydrides with long chain fatty acids condensed with ethylene oxide and mixtures thereof.

6. A cosmetic composition comprising:
   (i) a skin whitening agent comprising:
      (a) one or more sucrose esters of lauric acid;
      (b) an extract of *Pisum sativum* obtained with water heated at 45-50° C.; and
      (c) optionally, one or more additional skin-whitening actives;

wherein the ratio of the sucrose esters of lauric acid to the extract is 10:1 based on a dry weight basis, and the extract is present in an amount effective to increase the tyrosinase inhibiting efficacy of the sucrose esters of lauric acid; and (ii) one or more components selected from the group consisting of mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, hydrotropes, solubilizers, preservatives, perfume oils, dyes, and water.

7. The cosmetic composition of claim 6, wherein said skin whitening agent (i) is present in a concentration of from about 0.1 to about 10 weight-% based on the total components of the cosmetic composition.

8. The cosmetic composition of claim 7, wherein said composition comprises 0.1% to 5% w/w of the skin whitening agent.

9. The cosmetic composition of claim 7, wherein said composition comprises 2.5% w/w of the skin whitening agent.

10. A method for whitening skin in a subject in need thereof, comprising topically applying to skin of said subject an effective amount of the composition of claim 6, wherein said effective amount induces skin whitening.

11. A method for whitening skin in a subject in need thereof, comprising topically applying to skin of said subject an effective amount of the skin whitening agent of claim 1, wherein said effective amount induces skin whitening.

* * * * *